United States Patent [19]

Harris

[11] Patent Number: 4,487,603
[45] Date of Patent: Dec. 11, 1984

[54] IMPLANTABLE MICROINFUSION PUMP SYSTEM

[75] Inventor: Donald L. Harris, Miami Beach, Fla.

[73] Assignee: Cordis Corporation, Miami, Fla.

[21] Appl. No.: 444,383

[22] Filed: Nov. 26, 1982

[51] Int. Cl.³ ............................................. A61M 5/00
[52] U.S. Cl. ................................. 604/152; 417/417;
128/DIG. 12; 604/891
[58] Field of Search ................. 604/65, 891, 131, 151,
604/152; 128/DIG. 12; 417/417, 418, 566;
222/333, 383, 370

[56] References Cited

U.S. PATENT DOCUMENTS

| | | | |
|---|---|---|---|
| 3,250,219 | 5/1966 | McCarty et al. | 417/566 X |
| 3,486,456 | 12/1969 | Hager et al. | 417/417 |
| 4,013,074 | 3/1977 | Siposs | 604/891 |
| 4,360,019 | 11/1982 | Portner et al. | 604/891 |
| 4,413,950 | 11/1983 | Wiernicki | 417/417 X |
| 4,447,233 | 5/1984 | Mayfield | 604/152 |
| 4,447,234 | 5/1984 | Mayfield | 604/152 |

Primary Examiner—Stephen C. Pellegrino
Attorney, Agent, or Firm—Henry W. Collins; Eugene M. Cummings

[57] ABSTRACT

An implantable microinfusion pump system for dispensing medication at a prescribed infusion rate within the human body includes a hermetically sealed housing in which a power source and circuitry for actuating the pump are contained. A permanently magnetized piston is mounted for reciprocative fill and pump strokes within a pump chamber defined by a pump body member which extends between parallel-spaced walls of the housing. The body member communicates at one end with an expandable medicament reservoir adjacent one wall of the housing, and at the other end with a catheter for conveying medicament to the body. A two stage valve arrangement causes medicament to enter the pump chamber during fill strokes of short duration and to be dispensed from the pump chamber at the prescribed infusion rate during longer duration pump strokes. To minimize current drain from the power source the piston is driven through the shorter duration fill strokes by magnetic actuator windings within the housing, and through the longer duration pump strokes by magnetic attraction between the piston and a magnetic pole piece.

18 Claims, 9 Drawing Figures

IMPLANTABLE MICROINFUSION PUMP SYSTEM

BACKGROUND OF THE INVENTION

The present invention is directed generally to infusion systems, and more particularly to an implantable microinfusion pump system for dispensing a fluid medicament at a prescribed rate within the human body over an extended period of time.

Implanted microinfusion pump systems are advantageously employed where a medicament is to be dispensed to an ambulatory patient on a regular basis over an extended period of time, as where insulin is dispensed in the treatment of diabetes, or where chemotherapeutic drugs are dispensed in the treatment of cancer. In performing these and other internal body procedures such pump systems must be reliable in operation, must be sealed against body fluids, must hold a sufficient quantity of medication so as to avoid the need for frequent refills, and must be refillable when nearly empty to preclude interruption of the medication schedule. Furthermore, such pump systems must be physically small so as to be readily implantable without unnecessary disturbance to the body, and must be operable on their own internal batteries for a sustained period of time.

One drawback of previous implantable microinfusion pump systems has been the relatively short life of the pump batteries because of the extended current demand of the pump actuator circuitry while dispensing the relatively slow moving medicament. The microinfusion system of the present invention overcomes this drawback by limiting current demand to a refill stroke of short duration, the pump stroke being accomplished by a permanent magnet at a rate compatible with the desired medication delivery rate.

Another drawback of previous implantable pumps has been the undesirably large size and complexity of the pump housings. The pump system of the present invention utilizes a compact hermetically sealed housing wherein the pump mechanism is positioned within a pump body member which extends between opposite parallel-spaced walls of the housing. The batteries and circuitry for actuating the pump are contained within the housing, which is formed to provide in conjunction with an adjacent flexible wall a reservoir for medicament to be infused.

Still another drawback of previous microinfusion pumps has been that their valving arrangements were undesirably subject to wear with extended use, and did not prevent uncontrolled flow of medicament when the pump apparatus was subjected to high external pressures. The present invention provides a valve arrangement which minimizes friction between the pump piston and valve surfaces, thereby minimizing wear, and which provides positive protection against uncontrolled flow of medicament in the event of externally applied pressures.

SUMMARY OF THE INVENTION

Accordingly, it is a principal object of the present invention to provide a new and improved implantable microinfusion pump system.

It is another object of the invention to provide an implantable microinfusion pump system which is compact and reliable, and which has improved battery life.

It is another object of the invention to provide an implantable microinfusion pump system which has improved resistance to wear and reduced susceptibility to uncontrolled fluid flow in response to externally applied pressures.

It is another object of the invention to provide an implantable microinfusion pump system wherein refill strokes are accomplished over short time intervals by periodic actuation of a magnetic winding, and pump strokes are accomplished over extended intervals by the magnetic attraction of a permanent magnet.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
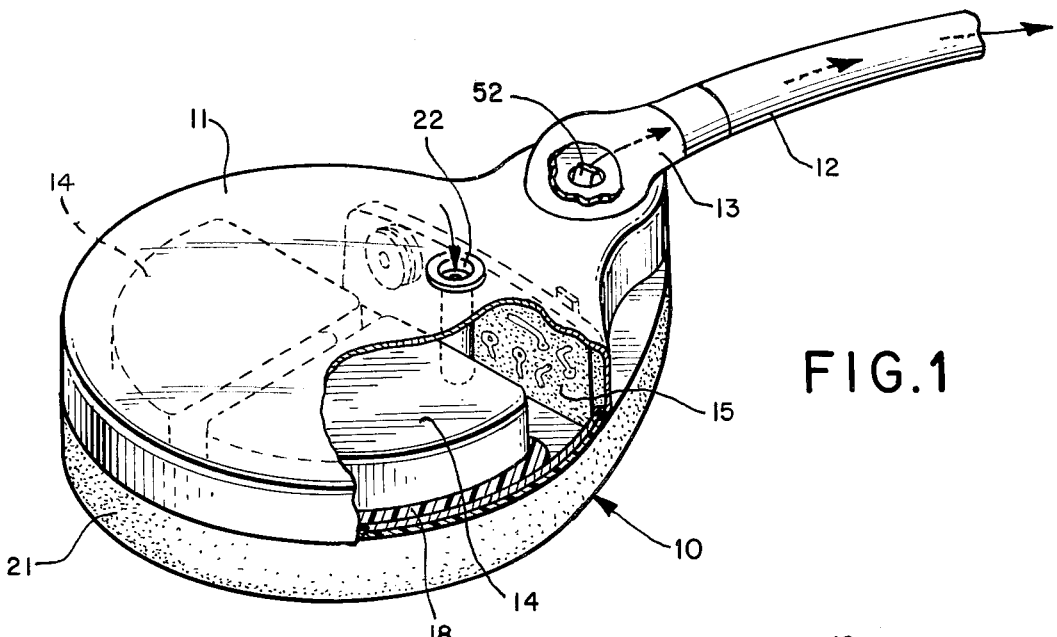
FIG. 1 is an enlarged perspective view of an implantable microinfusion pump system constructed in accordance with the invention partially broken away to show the internal battery supply and actuator circuitry of the system.
Figures 2, 3:
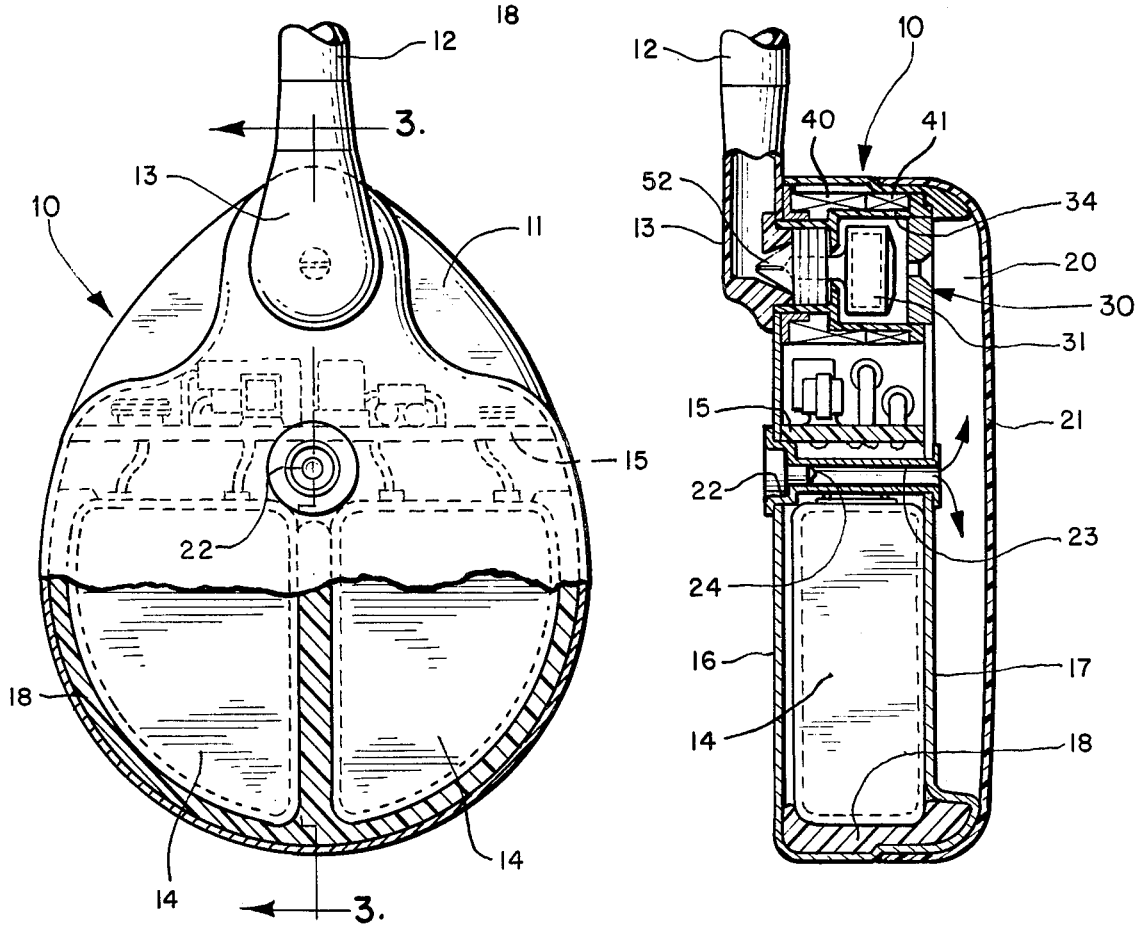
FIG. 2 is a top plan view of the microinfusion pump system of FIG. 1 partially broken away to show certain internal components thereof.
FIG. 3 is a cross-sectional view of the microinfusion pump system taken along line 3—3 of FIG. 2.

Referring to the Figures, and particularly to FIGS. 1-3, an implantable microinfusion pump system 10 constructed in accordance with the invention is seen to comprise a hermetically sealed housing 11 formed of titanium or other suitable material non-reactive with the human body. Medicament is conveyed from the pump system 10 by means of a catheter 12 which may be conventional in construction and which may be attached to an outlet fitting 13 of the pump system by conventional attachment means.

Within housing 11 the microinfusion pump system includes a power source in the form of a pair of conventional lithium batteries 14 arranged side-by-side and appropriately interconnected. These batteries supply operating power to pump control and actuator circuitry mounted on a circuit board 15 within the housing.

As seen in FIG. 3, pump housing 11 may be formed by two generally parallel-spaced walls 16 and 17 joined together at their ends by welding or other appropriate bonding techniques to form a sealed internal chamber 18. Although shown as a generally kidney-shaped housing in the figures, it will be appreciated that this housing may take various shapes and forms as appropriate to the implantation procedure to which it is intended. For example, the housing may be formed in a round shape or in a rectangular shape.

To provide for an integral source of medicament, a medicament reservoir 20 is formed adjacent wall 17 by means of a flexible and resilient expandable wall 21, fastened about its periphery to wall 17. The intervening volume between wall 17 and wall 21 forms a reservoir in which the medicament is contained. When the housing is implanted, fluid pressure within the body exerts pressure on wall 21, tending to deform the wall inwardly and thereby pressurize liquid medicament contained within reservoir 20. The rigid adjacent wall 17 of housing 11, in accordance with the one aspect of the invention, serves to protect the reservoir from being punctured by externally inserted needles, as when the reservoir is being refilled.

To provide for refilling reservoir 20, the pump system 10 includes an inlet port 22. As shown in FIG. 3, the inlet port 22 is formed by a hollow tube 23 which extends through the housing between walls 16 and 17. The tubing segment 23, which may be formed of titanium or other material compatible with housing 11, preferably includes flange portions in either end which are welded to respective walls 16 and 17 of the housing to maintain the interior of the housing hermetically sealed from the environment. A needle stopper 24 of conventional construction within tube 23 allows medicament to be introduced into the reservoir by introducing an appropriate catheter and needle at inlet 22 by means of well known surgical procedures. Stopper 24 also functions as a check valve to prevent medicament within the reservoir from flowing out through tube 23.

Figure 4:
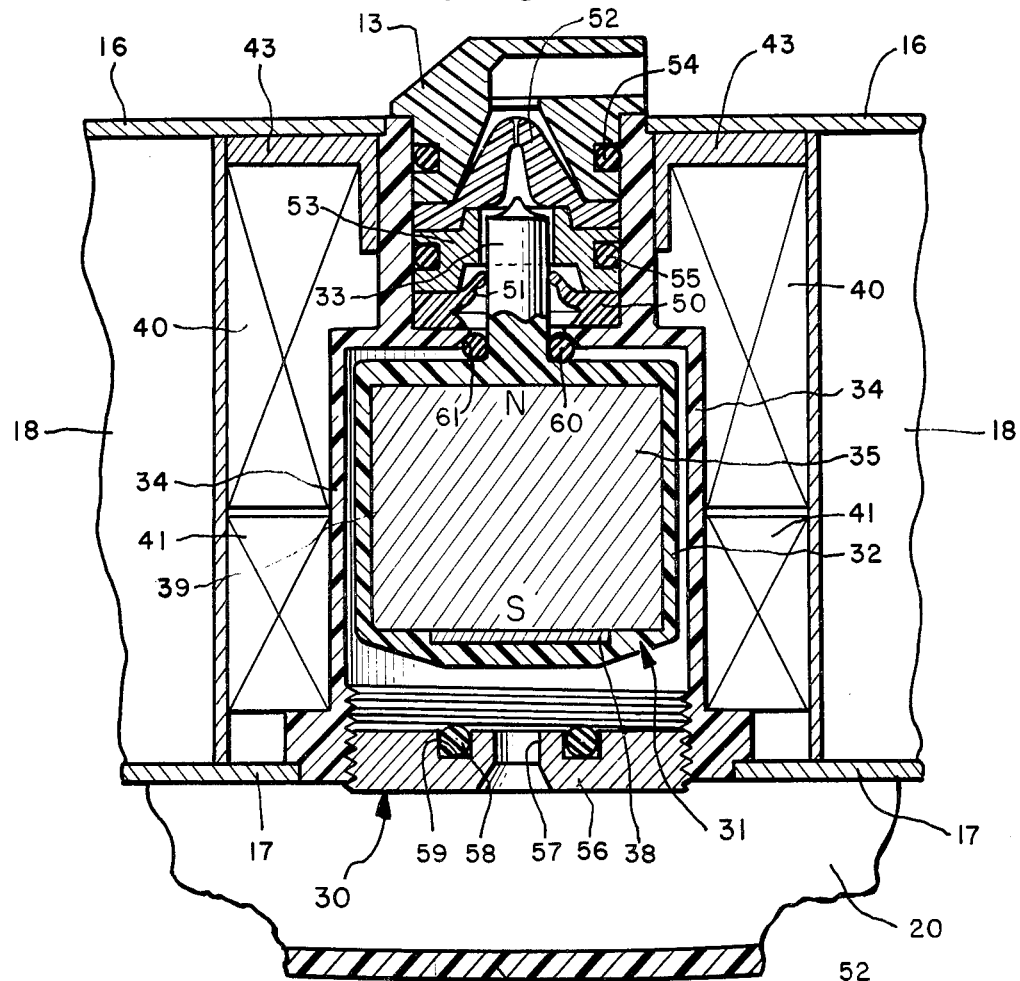
FIG. 4 is an enlarged cross-sectional view of the pump portion of the microinfusion pump system taken along line 4—4 of FIG. 3 showing the piston and valve construction thereof.

Medicament is introduced from reservoir 20 into the body through catheter 12 by means of an electromagnetically-actuated pump assembly 30 in fluid communication with reservoir 20 and outlet port 13. Referring to FIG. 4, this pump assembly includes a piston 31 comprising a cylindrical body portion 32 of relatively large diameter, and a stem portion 33 of relatively small diameter. The piston is mounted for reciprocative movement within a pump chamber defined by a pump body member 34 having an enlarged diameter portion for slidably receiving the body portion 32 of piston 31, and a reduced diameter portion for receiving the stem portion of piston 31. Body member 34, which is preferably formed of titanium or another non-magnetic material compatible with system housing 11, extends between housing walls 16 and 17 and is welded at its ends to the walls to maintain the interior of the system housing hermetically sealed.

Piston 31 is actuated in alternate downward fill strokes, and upward pump strokes, by means of a rare earth permanent magnet 35 of annular cross-section disposed within the enlarged body portion 32 of piston 31, in conjunction with a pair of magnetic windings 40 and 41, and a magnetic pole piece 43. As shown in FIG. 4, the permanent magnet is positioned in axial alignment with the piston stem portion 33, the body portion 32 comprising a molding of plastic, titanium, or other suitable material coated over the magnet. An end plate 38 may be provided adjacent the outwardly projecting end of magnet 35 to concentrate the magnetic flux produced by the magnet.

Movement of piston 31 in the alternate fill strokes is obtained by energization of the two magnetic actuator windings 40 and 41 which are arranged in concentric relationship to the piston on pump body member 34 so as to be contained within the hermetically sealed interior 18 of the housing. Winding 40 is located adjacent stem portion 33 and is dimensioned to accommodate the increased-diameter body portion of the valve housing. The magnetic pole piece 43, which is seen to be of generally annular form, includes an inwardly projecting annular sleeve portion which fits over the pump body member 34 between the body member and magnetic winding 40. This magnetic pole piece is formed of a soft magnetic material, such as soft iron, so as to have a low magnetic reluctance, and hence a high magnetic interaction with the permanent magnet 35 of piston 31.

Figure 5A:
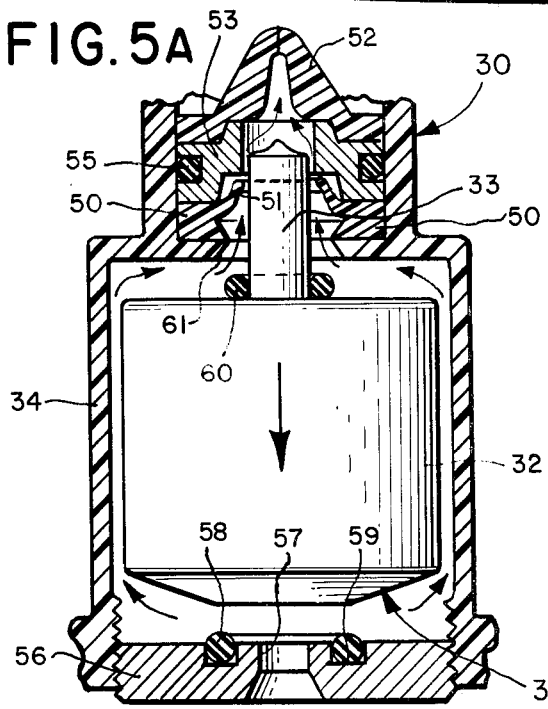
FIG. 5a is a cross-sectional view of the pump portion of the microinfusion pump system showing the principal components of the pump during its fill stroke.
Figure 5B:
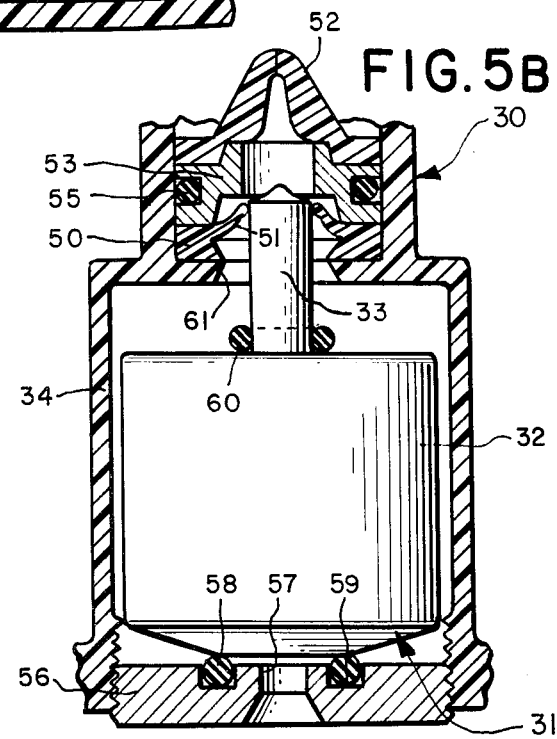
FIG. 5b is a cross-sectional view similar to FIG. 5a showing the pump at the completion of its fill stroke.

Upon application of an electric current to magnetic actuator windings 40 and 41 piston 31 is driven downwardly (as seen in FIGS. 5a and 5b) as a result of the force exerted on permanent magnet 35 by the magnetic flux produced by windings 40 and 41. In particular, energization of magnetic windings 40 and 41 results in the formation of a magnetic field which includes a north magnetic pole at the end of the sleeve portion of pole piece 43. This interacts with the magnetic North pole of permanent magnet 35 to repel the magnet, driving piston 31 downwardly as the magnet attempts to accommodate the magnetic field. Since there is little opposition to downward movement of the piston, the downward stroke is accomplished quickly, and windings 40 and 41 need be energized only momentarily to minimize energy consumption from the system batteries.

Upon completion of the downward fill stroke and deenergization of windings 40 and 41, the magnetic force field generated by windings 40 and 41 is no longer present, and only the magnetic attraction of magnet 35 to pole piece 43 as the magnet attempts to accommodate its magnetic flux remains to act on piston 31. In accordance with one aspect of the invention, this magnetic force causes piston 31 to be attracted toward the pole piece and to move upwardly, thereby accomplishing a pump stroke. Since no current is consumed from the battery during upward movement of the piston, the pump stroke may be accomplished over an extended period compatible with the prescribed infusion rate of the medicament, without depletion of the system batteries.

Figure 6:
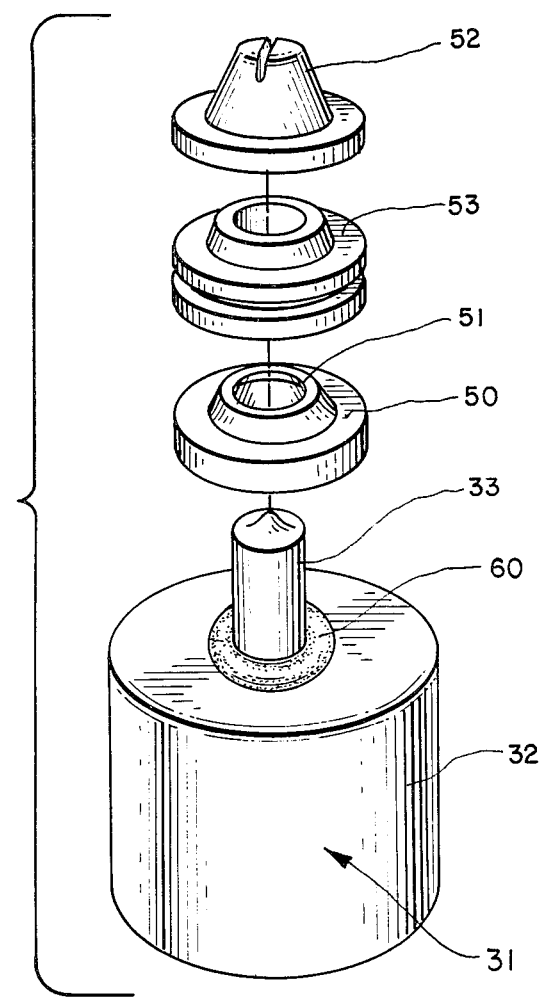
FIG. 6 is an exploded perspective view of the principal elements of the pump portion of the microinfusion pump system.

Referring to FIG. 6, to provide fluid metering action with reciprocative movement of piston 31, the pump assembly 30 includes within pump housing member 34, in accordance with another aspect of the invention, an annular sleeve-type valve 50 having a deformable radially projecting annular flange 51 which engages the surface of the stem portion 33 of piston 31, and a slit-type valve 52, which is normally biased closed and opens only upon application of fluid pressure from within the pump chamber to allow fluid to flow through outlet fitting 13. An annular spacer element 53 maintains a predetermined fixed spacing between the valve members along the pump axis. A pair of annular O-ring members 54 and 55 provide a fluid seal between the valve members.

In operation, in an initial rest position, following completion of a pump stroke and prior to initiation of a fill stroke, valve members 50 and 52 are closed, as shown in FIG. 4. At this time no medicament flow takes place, and the volume of medicament contained within the pump chamber is minimized by reason of the stem portion 33 of piston 31 generally conforming to the conical inside surface of the slit valve 52.

Upon subsequent energization of magnetic actuator windings 40 and 41, the interaction between the magnetic field produced by the windings and permanent magnet 35 causes piston 31 to accomplish a fill stroke, as shown in FIG. 5b. During this fill stroke medicament contained in the pump chamber flows freely around the sides of the downwardly moving piston (which fits loosely within pump housing 34 to permit such flow) toward stem portion 33. As the medicament flows it causes the annular sleeve 51 of valve member 50 to be radially outwardly deflected as shown, enabling the medicament to continue to a location in the pump chamber above stem portion 33. Since insufficient pressure is exerted on slit valve 52 during the fill stroke to open the valve, the slit valve remains closed and the medicament is confined to the space between the slit valve and the end of stem portion 33.

Upon completion of the fill stroke piston 31 comes into abuttment with an end cap 56, which may be threaded onto the open end of the pump body member 34. An aperture 57 in the end cap provides fluid communication between reservoir 20 and the pump chamber. To provide for a noise free positive stop between piston 31 and end cap 56, the valve assembly preferably includes an O-ring 58 which engages the bottom end of the piston at the completion of the fill stroke. O-ring 58 is preferably contained within a channel 59 provided on the inside surface of end cap 56 and is of appropriate dimensions to engage the piston around the entire circumference of aperture 57.

Figure 5C:
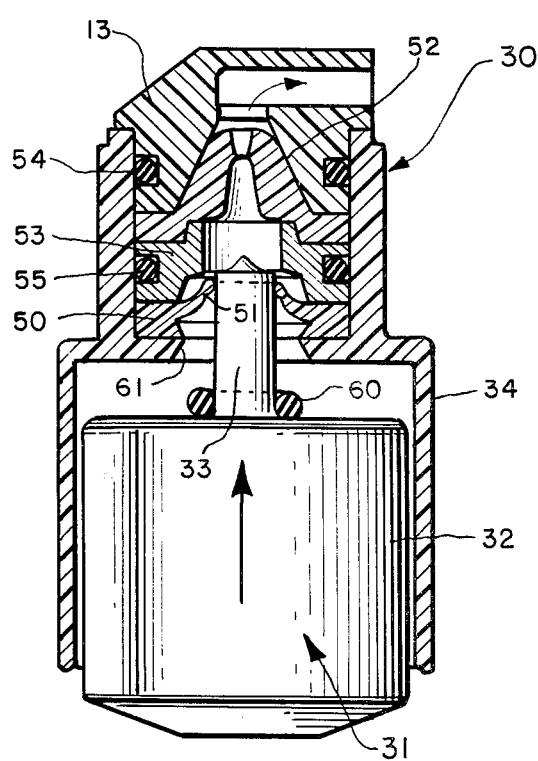
FIG. 5c is a cross-sectional view similar to FIG. 5a showing the pump during its pump stroke.

Upon completion of the fill stroke valve members 50 and 52 close and the medicament to be infused is enclosed above stem portion 33, as shown in FIG. 5b. Upon occurrence of the subsequent pump stroke, as shown in FIG. 5c, piston 31 moves upwardly and causes the medicament trapped above stem portion 33 to force slit valve 50 open and to advance through catheter 12 for introduction into the patient. The pressure of the medicament trapped above the stem tends to force the annular sleeve sliding valve 50 against the piston stem 33, acting as a check valve to prevent back flow. Friction generated by this force is minimal since the forward movement of the piston tends to push the ring outward, minimizing wear between the annular ring and the surface of the stem. Upward movement of piston 31 continues until the completion of the pump stroke, at which time valves 50 and 52 are again closed and the piston is positioned as shown in FIG. 4.

To prevent uncontrolled flow of medicament as a result of excessive external compression forces being applied to the flexible wall 21 of reservoir 20, the base of plunger stem portion 33 includes, in accordance with another aspect of the invention, sealing means in the form of an O-ring 60. In the event of excessive pressure, the increased medicament pressure forces piston 31 upward, bringing O-ring 60 to bear against an inclined valve surface 61 on pump body member 34. This effectively seals the passage along stem portion 33, preventing medicament from advancing through valves 50 and 52 to catheter 12.

Figure 7:
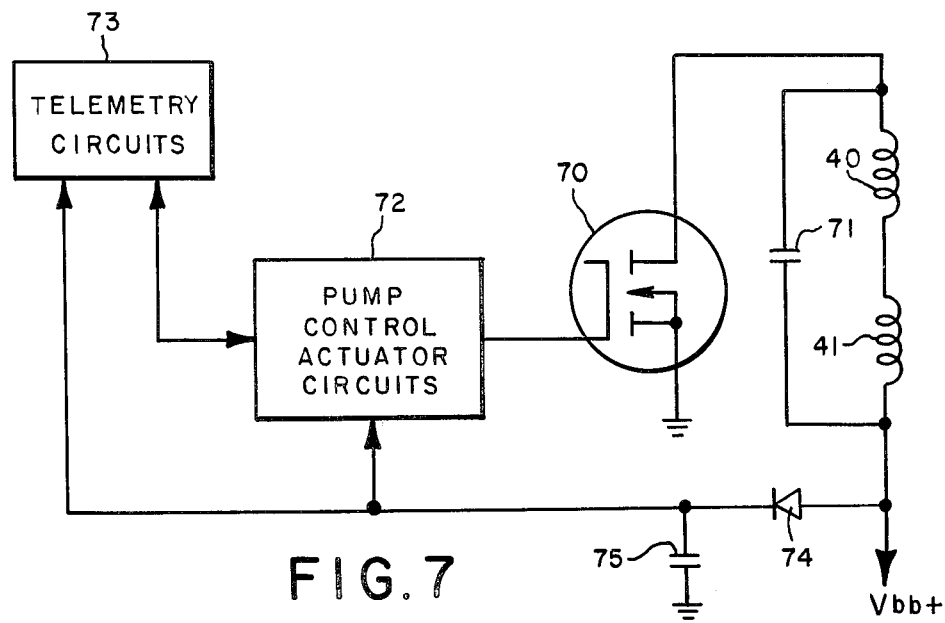
FIG. 7 is a simplified schematic diagram partially in functional block form of the pump control and actuator circuit employed in the microinfusion pump system of FIG. 1.

Magnetic windings 40 and 41 are periodically energized by circuitry contained within the hermetically sealed interior 18 of system 11. Referring to FIG. 7, the application of current from batteries 14 to actuator windings 40 and 41 is controlled by switching means in the form of an N-type MOS transistor 70 connected in series with the windings and the battery. A capacitor 71 is connected across the windings.

Transistor 70 is periodically rendered conductive by a control pulse developed by a pump control circuit 72. This control circuit, which is preferably a miniature digital circuit having low power consumption, includes necessary time base circuitry to generate control pulses in accordance with a desired medication administration schedule. The schedule may be permanently set at the time of implantation, or preferably may be subsequently set and modified as necessary by means of a telemetry circuit 73 responsive to externally applied radio or magnetic signals, in accordance with conventional practice. This enables the administration rate of the medicament to be increased when necessary, as for example, in the case of insulin administration, after the patient has consumed a meal. In addition, the telemetry circuit may provide communication back to an attending physician confirming operation of the pump in accordance with telemetered instructions.

Operating power for circuits 72 and 73 is obtained from the system batteries 14. To this end, a diode 74 is connected between the batteries and the circuits. A filter capacitor 75 may be provided between the diode and system ground.

In practice, the system circuitry may be incorporated in one or more integrated circuits including necessary memory, logic, communication and control circuits to accomplish actuation and control of the pump system. Since an exact predetermined volume of medicament equal to the pump chamber volume between piston stem portion 32 and slit valve 50 is dispensed with each pump stroke, and since the number of pump strokes in a given time interval may be controlled with great accuracy, the pump system provides a highly accurate means for delivering medicament to the human body.

Furthermore, the pump apparatus is compact and reliable, being constructed within a hermetically sealed housing which precludes contamination of the pump actuator circuitry and power source by body fluids. The pump mechanism is of unique design, utilizing a multi-stage valving arrangement which minimizes wear with extended use of the pump and precludes uncontrolled flow as a consequence of externally applied pressures.

Battery consumption is minimized as a result of the utilization of battery power only to accomplish a rapid fill stroke, and the utilization of the attractive force of a permanent magnet to complete an extended pump stroke at a rate compatible with fluid flow through the catheter.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A microinfusion pump system for administering a fluid to the human body at a predetermined rate, comprising:
   a housing defining a pump chamber;
   a piston including a permanent magnet mounted for reciprocative movement in said pump chamber in a first direction comprising a pump stroke;

valve means in said pump chamber responsive to reciprocation of said piston for urging fluid through said pump chamber, movement of said piston in one direction comprising a fill stroke for admitting fluid into said chamber, and movement of said piston in an opposite direction comprising a pump stroke for forcing fluid from said chamber;

a magnetic actuator winding in magnetic communication with said piston;

circuit means including said magnetic actuator winding for periodically actuating said magnetic winding to drive said piston along said fill stroke; and said permanent magnet coacting with said housing to drive said piston through said pump stroke upon termination of said fill stroke to meter fluid from said pump housing.

2. A microinfusion pump system as defined in claim 1 wherein said housing includes a magnetic pole member of low magnetic retention capability, and said permanent magnet coacts with said pole piece to drive said piston through said pump stroke.

3. A microinfusion pump system as defined in claim 1 wherein said magnetic pole piece is formed of soft magnetic material.

4. A microinfusion pump system as defined in claim 1 wherein the magnetic poles of said permanent magnet are aligned with the axis of said piston.

5. A microinfusion pump system as defined in claim 1 wherein said magnetic winding is concentric with the axis of said piston.

6. A microinfusion pump system as defined in claim 1 wherein said actuator means include a pair of magnetic actuator windings arranged in magnetic communication with said permanent magnet.

7. A microinfusion pump system as defined in claim 1 wherein said valve means comprise a sleeve-type valve engaging the surface of said piston, and a slit-type valve at the outlet end of said pump housing.

8. A microinfusion pump system for infusing a fluid into the human body at a predetermined rate, comprising:

a housing including parallel-spaced walls defining a sealed compartment within;

means comprising a pump body member extending between said parallel-spaced walls, said body member defining a pump chamber;

valve means including a piston having a permanent magnet mounted for reciprocative movement within said pump chamber;

valve means in said pump chamber responsive to reciprocative movement of said piston for urging fluid through said pump chamber, movement of said piston in one direction comprising a fill stroke admitting fluid to said pump chamber, and movement of said piston in the opposite direction comprising a pump stroke for forcing fluid from said chamber;

a magnetic actuator winding in magnetic communication with said piston;

circuit means including said magnetic actuator winding for periodically actuating said winding to drive said piston along said fill stroke; and said permanent magnet coacting with said housing to drive said piston through said pump stroke upon termination of said fill stroke to meter fluid from said pump housing.

9. A microinfusion pump system as defined in claim 8 wherein said housing is formed of titanium.

10. A microinfusion pump system as defined in claim 8 wherein said pump body member is welded to said parallel-spaced walls of said compartment.

11. A microinfusion pump system as defined in claim 8 including a fluid reservoir adjacent one of said walls, said pump chamber being in fluid communication with the interior of said reservoir.

12. A microinfusion pump system as defined in claim 8 wherein said magnetic actuator winding is concentric with the axis of said piston.

13. A microinfusion pump system as defined in claim 8 wherein said pump body member is of annular cross-section.

14. A microinfusion pump for infusing a fluid into the human body at a predetermined rate, comprising:

a housing defining a pump chamber;

a piston including a permanent magnet mounted for reciprocative movement in said pump chamber;

valve means responsive to said reciprocative movement of said piston for urging fluid through said pump chamber, movement of said piston in one direction comprising a fill stroke admitting fluid to said chamber, and movement of said piston in the opposite direction comprising a pump stroke for forcing fluid from said chamber, said valve means comprising an annular flange resiliently biased into engagement with the side wall of said piston, and being forced out of engagement with said side-wall by fluid in said pump chamber when said piston is in motion, said valve means including an additional valve at the outlet end of said pump chamber allowing flow only in a direction from said chamber; and circuit means including a magnetic winding for periodically initiating reciprocative movement of said piston to meter fluid through said pump chamber.

15. A microinfusion pump system as defined in claim 14 wherein said annular flange valve comprises a sleeve-type valve of annular cross-section.

16. A microinfusion pump system as defined in claim 15 wherein said additional valve comprises a slit-type valve.

17. A microinfusion pump system for infusing a fluid into the human body at a predetermined rate, comprising:

a housing defining a pump chamber;

a piston including a permanent magnet mounted for reciprocative movement in said pump chamber;

valve means in said pump chamber responsive to reciprocation of said piston for urging fluid through said pump chamber, movement of said piston in one direction comprising a fill stroke admitting fluid to said chamber, and movement of said piston in the opposite direction comprising a pump stroke for forcing fluid from said chamber, said valve means comprising additional valve means at one end of said pump chamber for preventing flow through said valve chamber when said piston is at said end of said chamber; and circuit means including a magnetic actuator winding for periodically initiating reciprocative movement of said piston to meter fluid through said pump chamber.

18. A microinfusion pump system as defined in claim 17 wherein said additional valve means comprise an annular O-ring engaging said piston.

* * * * *